US012364670B2

(12) United States Patent
Guy et al.

(10) Patent No.: US 12,364,670 B2
(45) Date of Patent: Jul. 22, 2025

(54) CANNABIDIOL-TYPE CANNABINOID COMPOUND

(71) Applicant: JAZZ PHARMACEUTICALS RESEARCH UK LIMITED, Sittingbourne (GB)

(72) Inventors: Geoffrey Guy, Cambridge (GB); Volker Knappertz, Cambridge (GB); Benjamin Whalley, Cambridge (GB); Marie Woolley-Roberts, Cambridge (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 600 days.

(21) Appl. No.: 17/777,677

(22) PCT Filed: Nov. 18, 2020

(86) PCT No.: PCT/GB2020/052936
§ 371 (c)(1),
(2) Date: May 18, 2022

(87) PCT Pub. No.: WO2021/099775
PCT Pub. Date: May 27, 2021

(65) Prior Publication Data
US 2023/0026079 A1    Jan. 26, 2023

(30) Foreign Application Priority Data

Nov. 19, 2019 (GB) .................................... 1916849

(51) Int. Cl.
*A61K 31/05*     (2006.01)
*A61K 31/65*     (2006.01)
*A61P 25/08*     (2006.01)

(52) U.S. Cl.
CPC .............. *A61K 31/05* (2013.01); *A61P 25/08* (2018.01)

(58) Field of Classification Search
CPC ........ A61K 31/05; A61K 31/658; A61P 25/08
See application file for complete search history.

(56) References Cited

U.S. PATENT DOCUMENTS

| | | |
|---|---|---|
| 8,632,825 B2 | 1/2014 | Velasco Diez et al. |
| 8,790,719 B2 | 7/2014 | Parolaro et al. |
| 9,017,737 B2 | 4/2015 | Kikuchi et al. |
| 9,125,859 B2 | 9/2015 | Whalley et al. |
| 9,474,726 B2 | 10/2016 | Guy et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 10,583,096 B2 | 3/2020 | Guy et al. |
| 10,603,288 B2 | 3/2020 | Guy et al. |
| 10,709,671 B2 | 7/2020 | Guy et al. |
| 10,709,673 B2 | 7/2020 | Guy |
| 10,709,674 B2 | 7/2020 | Guy et al. |
| 10,765,643 B2 | 9/2020 | Guy et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,357,741 B2 | 6/2022 | Guy et al. |
| 11,400,055 B2 | 8/2022 | Guy et al. |
| 11,406,623 B2 | 8/2022 | Guy et al. |

(Continued)

FOREIGN PATENT DOCUMENTS

| | | |
|---|---|---|
| EP | 1476145 A1 | 11/2004 |
| WO | WO-0103690 A1 | 1/2001 |
| WO | WO-03070232 A1 | 8/2003 |
| WO | WO-2015193667 A1 | 12/2015 |

(Continued)

OTHER PUBLICATIONS

Epidiolex® (cannabidiol) oral solution, CV, Prescribing Information, 2018, 30 pages; https://www.accessdata.fda.gov/drugsatfda_docs/label/2018/210365lbl.pdf.
Jones, N. A. et al., Cannabidiol Displays Antiepileptiform and Antiseizure Properties In Vitro and In Vivo, J Pharmacol Exp Ther, 332(2):569-77 (2010). doi: 10.1124/jpet.109.159145. Epub Nov. 11, 2009.
Kimball, A. W. et al., Chemical Protection against Ionizing Radiation, Radiation Research, 7:1-12 (1957).
Lewis, M. M. et al., Chemical Profiling of Medical Cannabis Extracts, ACS Omega, 2:6091-6103 (2017).
Litchfield, J. T. & Wilcoxon, F., A simplified method of evaluating dose-effect experiments, J Pharmacol Exp Ther, 96(2):99-113 (1949).

(Continued)

*Primary Examiner* — Sahar Javanmard
(74) *Attorney, Agent, or Firm* — COOLEY LLP

(57) ABSTRACT

The present invention relates to a cannabidiol (CBD) type cannabinoid compound for use as a medicament. The CBD-type cannabinoid, cannabidiol-C6 (CBD-C6), is a naturally occurring cannabinoid that can be found in minor quantities in the cannabis plant. Furthermore, the cannabinoid can be produced by synthetic means and a method for the production of CBD-C6 is described herein. In addition, disclosed herein are data which demonstrate the efficacy of CBD-C6 in models of disease.

11 Claims, 2 Drawing Sheets

(56) References Cited

U.S. PATENT DOCUMENTS

| | | |
|---|---|---|
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy |
| 12,023,305 B2 | 7/2024 | Whalley et al. |
| 12,064,398 B2 | 8/2024 | Wright et al. |
| 12,064,399 B2 | 8/2024 | Guy et al. |
| 12,102,619 B2 | 10/2024 | Guy et al. |
| 2014/0298511 A1 | 10/2014 | Lewis et al. |
| 2015/0359756 A1 | 12/2015 | Guy et al. |
| 2017/0239193 A1 | 8/2017 | Guy et al. |
| 2018/0071210 A1 | 3/2018 | Wilkhu et al. |
| 2018/0228751 A1 | 8/2018 | Stott et al. |
| 2019/0167583 A1 | 6/2019 | Shah |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Knappertz |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0378714 A1 | 12/2022 | Guy et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy |
| 2023/0263744 A1 | 8/2023 | Guy |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig |
| 2023/0372367 A1 | 11/2023 | Checketts et al. |
| 2023/0372368 A1 | 11/2023 | Checketts et al. |
| 2024/0016819 A1 | 1/2024 | Craig |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 3/2024 | Guy et al. |
| 2024/0130981 A1 | 4/2024 | Wilkhu |
| 2024/0131041 A1 | 4/2024 | Tse |
| 2024/0165048 A1 | 5/2024 | Guy |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse |
| 2024/0238218 A1 | 7/2024 | Silcock et al. |
| 2024/0254066 A1 | 8/2024 | Silcock et al. |
| 2024/0254072 A1 | 8/2024 | Silcock et al. |
| 2024/0261234 A1 | 8/2024 | Guy |
| 2024/0293762 A1 | 9/2024 | Loft et al. |

FOREIGN PATENT DOCUMENTS

| | | |
|---|---|---|
| WO | WO-2015193668 A1 | 12/2015 |
| WO | WO-2016094810 A2 | 6/2016 |
| WO | WO-2016203239 A1 | 12/2016 |
| WO | WO-2018061007 A1 | 4/2018 |
| WO | WO-2018205022 A1 | 11/2018 |
| WO | WO-2020069214 A2 | 4/2020 |
| WO | WO-2020232545 A1 | 11/2020 |

OTHER PUBLICATIONS

Loscher, W. et al., The role of technical, biological and pharmacological factors in the laboratory evaluation of anticonvulsant drugs. II. Maximal electroshock seizure models, Epilepsy Res., 8:79-94 (1991).

Pertwee, R. G., "The Pharmacology and Therapeutic Potential of Cannabidiol," Cannabinoids, Chapter 3, DiMarzo, V. (Ed.), pp. 32-83 (2004).

Rosenberg, E. C. et al., Therapeutic effects of cannabinoids in animal models of seizures, epilepsy, epileptogenesis, and epilepsy-related neuroprotection, Epilepsy & Behavior, 70:319-327 (2017).

Harvey, D. J., "Characterization of the Butyl Homologues of Delta1-tetrahydrocannabinol, Cannabinol and Cannabidiol in Samples of Cannabis by Combined Gas Chromatography and Mass Spectrometry," J. Pharm. Pharmac., 28:280-285 (1976).

Hill, T. D. M. et al., "Cannabidivarin-rich cannabis extracts are anticonvulsant in mouse and rat via a CB 1 receptor-independent mechanism," British Journal of Pharmacology, 170(3):679-692 (2013).

Morales, P. et al., "An Overview on Medicinal Chemistry of Synthetic and Natural Derivatives of Cannabidiol," Frontiers in Pharmacology, 8:422 (2017); doi:10.3389/fphar.2017.00422, 18 pages.

U.S. Appl. No. 15/640,033, filed Jun. 30, 2017.
U.S. Appl. No. 16/467,639, filed Jun. 7, 2019.
U.S. Appl. No. 16/768,241, filed May 29, 2020.
U.S. Appl. No. 16/959,350, filed Jun. 30, 2020.

(56) References Cited

OTHER PUBLICATIONS

U.S. Appl. No. 16/959,354, filed Jun. 30, 2020.
U.S. Appl. No. 16/959,357, filed Jun. 30, 2020.
U.S. Appl. No. 17/050,956, filed Oct. 27, 2020.
U.S. Appl. No. 16/935,005, filed Jul. 21, 2020.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/615,422, filed Nov. 30, 2021.
U.S. Appl. No. 17/552,487, filed Dec. 16, 2021.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/680,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,681, filed May 18, 2022.
U.S. Appl. No. 17/777,734, filed May 18, 2022.
U.S. Appl. No. 17/841,167, filed Jun. 15, 2022.
U.S. Appl. No. 17/786,949, filed Jun. 17, 2022.
U.S. Appl. No. 17/853,367, filed Jun. 29, 2022.
U.S. Appl. No. 17/816,349, filed Jul. 29, 2022.
U.S. Appl. No. 17/817,753, filed Aug. 5, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,868, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18,006,131, filed Jan. 19, 2023.
U.S. Appl. No. 18,006,133, filed Jan. 19, 2023.
U.S. Appl. No. 18/006,121, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.

Figure 1. Evaluation of Cannabidiol-C6 (CBD-C6) in the MEST test in the mouse
* P<0.05 P<0.01, * P<0.001 Significant change in threshold when compared to own vehicle
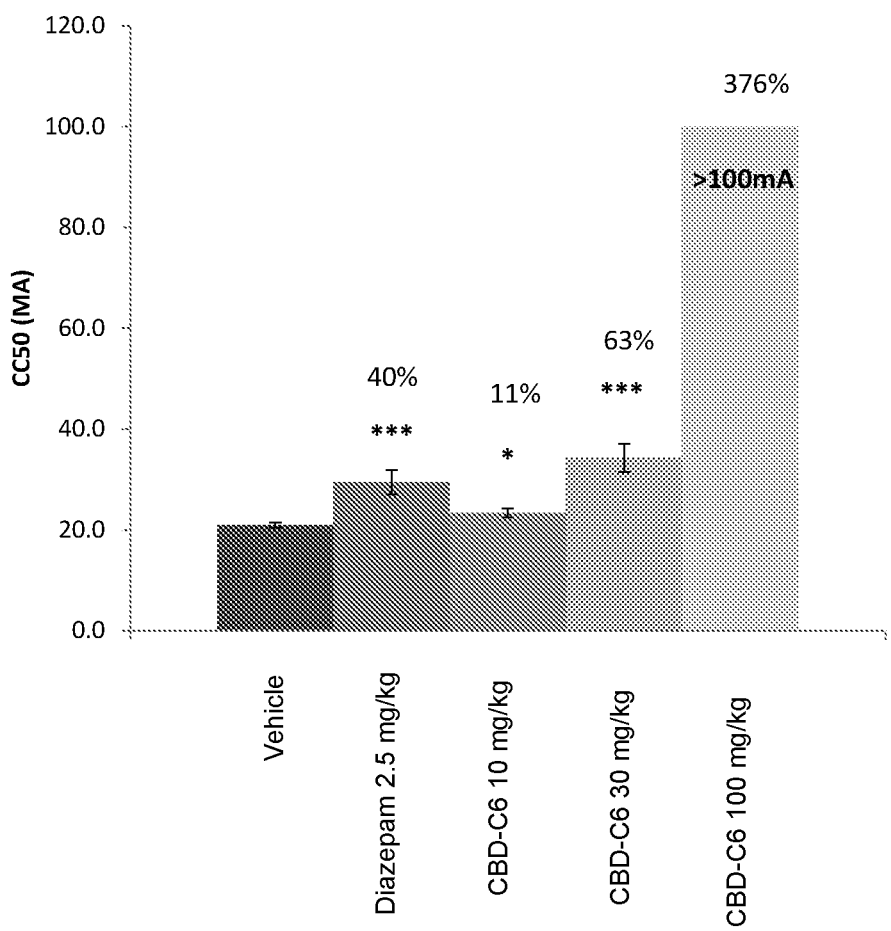

Figure 2. Effect of Cannabidiol-C6 (CBD-C6) on the electroshock-induced generalised seizure threshold (MEST) in the mouse
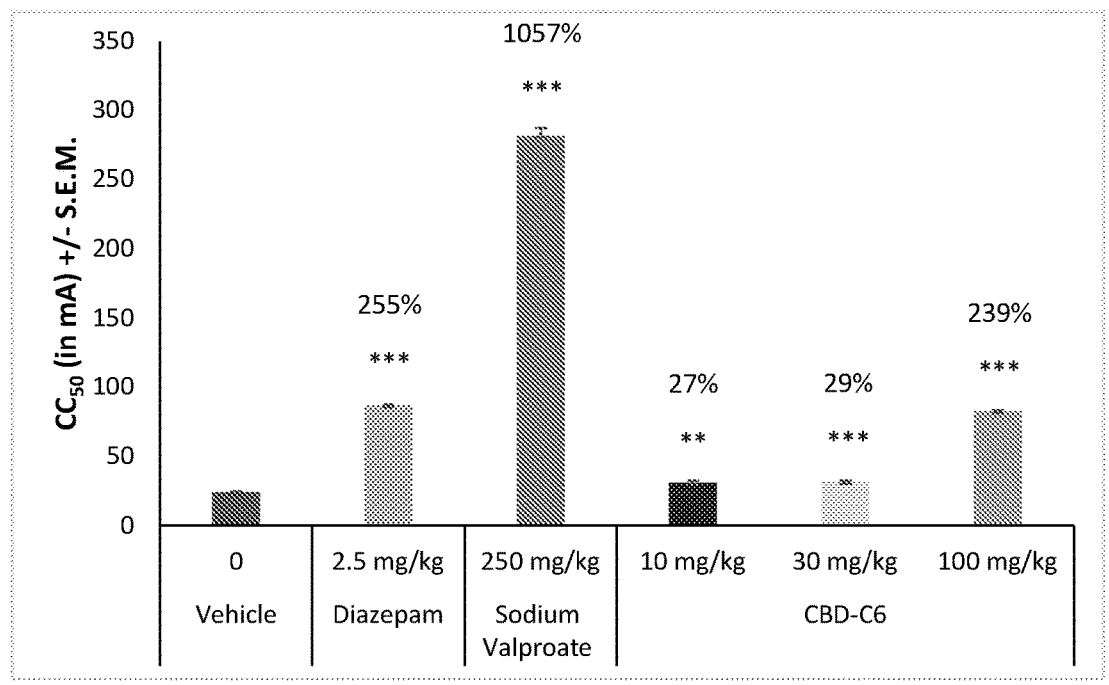
p<0.01 and *p<0.001 when compared to the vehicle group

CANNABIDIOL-TYPE CANNABINOID COMPOUND

CROSS-REFERENCE TO RELATED APPLICATIONS

This application is a U.S. National Phase application, field under U.S.C. § 371(c), of International Application No. PCT/GB2020/052936, filed Nov. 18, 2020, which claims priority to, and the benefit of, United Kingdom Patent Application No. 1916849.1, filed Nov. 19, 2019. Each of these documents is incorporated by reference herein in its entirety for all purposes.

FIELD OF THE INVENTION

The present invention relates to a cannabidiol (CBD) type cannabinoid compound for use as a medicament.

The CBD-type cannabinoid, cannabidiol-C6 (CBD-C6), is a naturally occurring cannabinoid that can be found in minor quantities in the cannabis plant. Furthermore, the cannabinoid can be produced by synthetic means.

Disclosed herein are data which demonstrate the efficacy of CBD-C6 in models of disease. In addition, a method for the production of CBD-C6 is described.

BACKGROUND TO THE INVENTION

Cannabinoids are natural and synthetic compounds structurally or pharmacologically related to the constituents of the cannabis plant or to the endogenous agonists (endocannabinoids) of the cannabinoid receptors CB1 or CB2. The only way in nature in which these compounds are produced is by the cannabis plant. Cannabis is a genus of flowering plants in the family Cannabaceae, comprising the species *Cannabis sativa, Cannabis indica*, and *Cannabis ruderalis* (sometimes considered as part of *Cannabis sativa*).

Cannabis plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPR5. The principle cannabinoids present in cannabis plants are cannabinoid acids $\Delta 9$-tetrahydrocannabinolic acid ($\Delta 9$-THCA) and cannabidiolic acid (CBDA) with small amounts of their respective neutral (decarboxylated) cannabinoids. In addition, cannabis may contain lower levels of other minor cannabinoids. "Chemical composition, pharmacological profiling, and complete physiological effects of these medicinal plants, and more importantly the extracts from cannabis, remain to be fully understood." Lewis, M. M. et al., ACS Omega, 2, 6091-6103 (2017).

Crude extracts from cannabis plants containing CBD have been used by patients suffering from diseases and disorders. However, such crude products are unsuitable for use in pharmaceutical formulations. Those seeking to prepare more consistent CBD preparations for use in treating diseases or disorders have made a concerted effort to either prepare CBD synthetically or attempt to remove all compounds other than CBD, particularly psychoactive compounds such as THC, from plant derived cannabinoids. See for example US 2014/0298511.

The present invention encompasses the surprising discovery that a minor cannabinoid related to CBD has therapeutic efficacy. This compound, cannabidiol-C1 (CBD-C1) can be extracted from the cannabis plant and purified or may be produced synthetically.

As stated, cannabinoids are a class of compounds which may be derived naturally from the cannabis plant or produced synthetically via chemical synthesis.

More than 100 different cannabinoids produced by cannabis have been identified. These cannabinoids can be split into different groups as follows: phytocannabinoids; endocannabinoids and synthetic cannabinoids (which may be novel cannabinoids or synthetically produced versions of phytocannabinoids or endocannabinoids).

Phytocannabinoids are cannabinoids that originate from nature and can be found in the cannabis plant. Phytocannabinoids can be isolated from plants to produce a highly purified extract. Phytocannabinoids may be obtained as either the neutral (decarboxylated form) or the carboxylic acid form depending on the method used to extract the cannabinoids from plant material. For example, it is known that heating the carboxylic acid form will cause most of the carboxylic acid form to decarboxylate into the neutral form. Phytocannabinoids can only be produced from plants, however versions of phytocannabinoids may be produced synthetically via chemical synthesis.

Endocannabinoids are endogenous lipid-based retrograde neurotransmitters that bind to cannabinoid receptors, and cannabinoid receptor proteins that are expressed throughout the mammalian central nervous system (including the brain) and peripheral nervous system. The endocannabinoid system is involved in regulating a variety of physiological and cognitive processes including fertility, pregnancy, during pre- and postnatal development, appetite, pain-sensation, mood, and memory, and in mediating the pharmacological effects of cannabis.

Synthetic cannabinoids are compounds that have a cannabinoid-like structure and are manufactured using chemical means rather than by the plant.

Certain cannabinoids are described in more detail below.

Cannabidiol (CBD) is a major cannabinoid constituent of Cannabis species, such as the hemp plant (*Cannabis sativa*). Unlike other cannabinoids, such as THC, cannabidiol does not bind CB1 or CB2, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

Cannabidiol administration has been the subject of research in an attempt to provide an alternative treatment for various diseases and disorders which may respond to such treatment.

Tetrahydrocannabinol (THC) is the principal psychoactive constituent of cannabis. THC is a partial agonist at the CB1 and CB2 receptors. Synthetic THC or dronabinol is approved for the treatment of loss of appetite in AIDS patients and nausea and vomiting caused by cancer chemotherapy.

Of the over 100 natural cannabinoids identified in *Cannabis sativa*, seven have been classified as CBD-type compounds, these cannabinoids have the same absolute configuration as CBD. These are: CBD, Cannabidiolic acid (CBDA), Cannabidivarin (CBDV), Cannabidivarin acid (CBDVA), Cannabidiol-C1 (CBD-C1), Cannabidiol-C4 (CBD-C4), Cannabidiol-C6 (CBD-C6) and Cannabidiol monomethyl ether (CBDM).

Cannabidiolic acid (CBDA) is the main form in which CBD exists in the cannabis plant. It is converted into CBD after decarboxylation.

Cannabidivarin (CBDV) is a homolog of CBD, with the side-chain shortened by two methylene bridges. CBDV is a non-psychoactive cannabinoid and has been shown to have anti-convulsant activity in a mouse model of epilepsy.

Cannabidiol-C1 (CBD-C1) also known as cannabidiorcol is a homolog of CBD, with the side-chain shortened by four methylene bridges. CBD-C1 occurs naturally in plants producing CBD but has not been shown to have any therapeutic effects.

Cannabidiol-C4 (CBD-C4) also known as nor-cannabidiol is a homolog of CBD, with the side-chain shortened by one methylene bridge. CBD-C4 occurs naturally in plants producing CBD and prior to the present invention has not been shown to have any therapeutic effects.

Cannabidiol-C6 (CBD-C6) is a homolog of CBD, with the side-chain increased by one methylene bridge. CBD-C6 may occur naturally in plants producing CBD and prior to the present invention has not been shown to have any therapeutic effects.

The present invention demonstrates data for the first time to indicate that the compound cannabidiol-C6 may have therapeutic benefit.

BRIEF SUMMARY OF THE DISCLOSURE

In accordance with a first aspect of the present invention there is provided cannabidiol-C6 (CBD-C6) for use as a medicament.

Preferably the CBD-C6 is in the form of a plant extract. More preferably the CBD-C6 is in the form of a highly purified extract of cannabis.

Preferably the highly purified extract comprises at least 80% (w/w) CBD-C6, more preferably the highly purified extract comprises at least 85% (w/w) CBD-C6, more preferably the highly purified extract comprises at least 90% (w/w), more preferably the highly purified extract comprises at least 95% (w/w) CBD-C6, more preferably still the highly purified extract comprises at least 98% (w/w) CBD-C6.

Alternatively, the CBD-C6 is present as a synthetic compound.

Preferably the dose of CBD-C6 is greater than 100 mg/kg/day. More preferably the dose of CBD-C6 is greater than 250 mg/kg/day. More preferably the dose of CBD-C6 is greater than 500 mg/kg/day. More preferably the dose of CBD-C6 is greater than 750 mg/kg/day. More preferably the dose of CBD-C6 is greater than 1000 mg/kg/day. More preferably the dose of CBD-C6 is greater than 1500 mg/kg/day.

Alternatively, the dose of CBD-C6 is less than 100 mg/kg/day. More preferably the dose of CBD-C6 is less than 50 mg/kg/day. More preferably the dose of CBD-C6 is less than 20 mg/kg/day. More preferably the dose of CBD-C6 is less than 10 mg/kg/day. More preferably the dose of CBD-C6 is less than 5 mg/kg/day. More preferably the dose of CBD-C6 is less than 1 mg/kg/day. More preferably the dose of CBD-C6 is less than 0.5 mg/kg/day.

In accordance with a second aspect of the present invention there is provided a composition for use as a medicament comprising cannabidiol-C6 (CBD-C6), and one or more pharmaceutically acceptable excipients.

In accordance with a third aspect of the present invention there is provided a cannabidiol-C6 (CBD-C6) for use in the treatment of epilepsy. Preferably the epilepsy is treated in a mammal. More preferably the mammal is a human. Alternatively, the mammal is a dog.

In accordance with a fourth aspect of the present invention there is provided a method for the production of cannabidiol-C6.

BRIEF DESCRIPTION OF THE DRAWINGS

Embodiments of the invention are further described hereinafter with reference to the accompanying drawings, in which:

FIG. 1 shows the effect of Cannabidiol-C6 (CBD-C6) in the MEST test in the mouse as described in Example 2.

FIG. 2 shows the effect of CBD-C6 on the electroshock-induced generalised seizure threshold (MEST) in the mouse as described in Example 3.

CANNABINOIDS AND THEIR ABBREVIATIONS

The cannabinoids described in the present application are listed below along with their standard abbreviations.

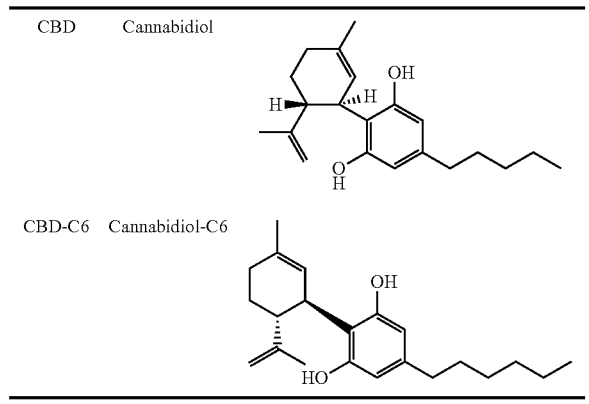

DETAILED DESCRIPTION

Example 1: Synthetic Production Method for Cannabidiol-C6 (CBD-C6)

As previously described the compound CBD-C6 may be produced as a minor cannabinoid in the cannabis plant. In a highly purified extract of cannabidiol the amount of CBD-C6 which remains in the extract is not more than 0.15% (w/w).

As such the synthetic pathway described below details a methodology that can be used in order to produce the cannabinoid CBD-C6 in larger quantities.

On the scheme R=C$_6$H$_{14}$

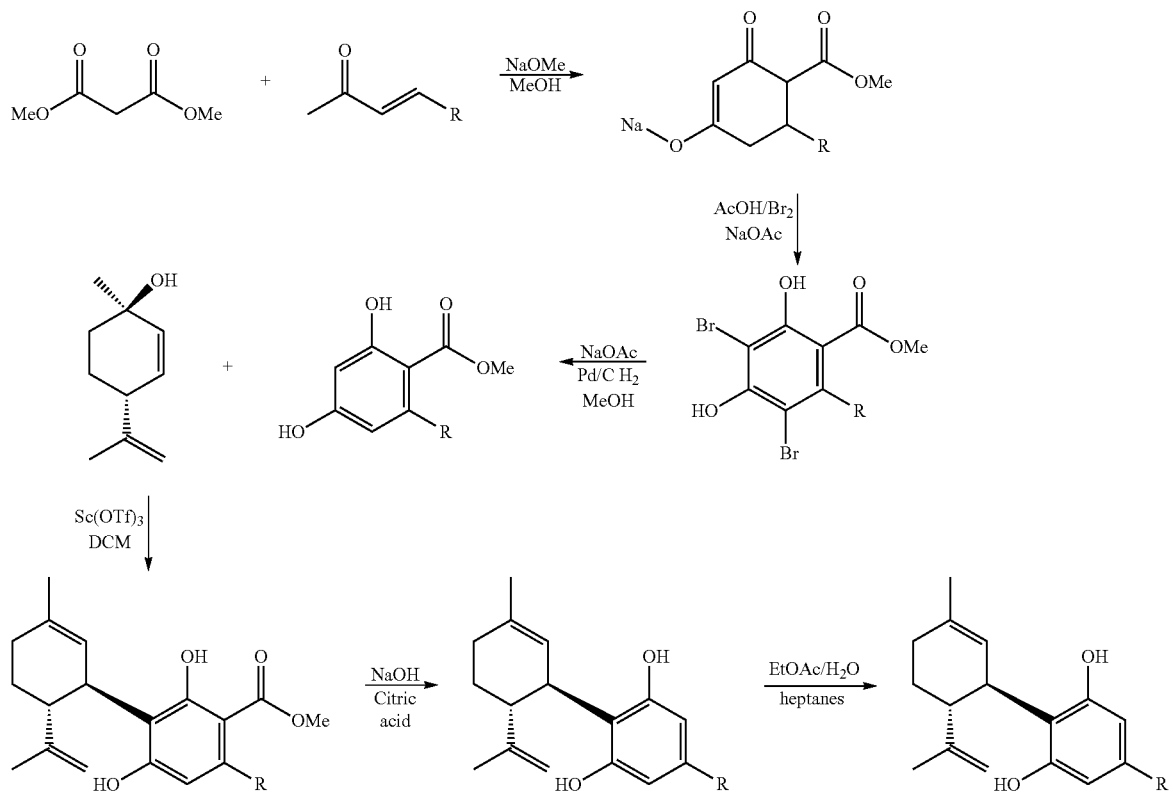

Example 2: Evaluation of Cannabidiol-C6 (CBD-C6) for Anticonvulsant Activity Using the Maximal Electroshock Seizure Threshold (MEST) Test in the Mouse The efficacy of CBD-C6 was tested in a mouse model of seizure, the maximal electroshock seizure threshold (MEST) test.

The maximal electroshock seizure threshold (MEST) test is widely utilized preclinically to evaluate pro- and anti-convulsant properties of molecules (Loscher et al., 1991).

In the MEST test the ability of a drug to alter the seizure threshold current required to induce hind limb tonic extensor convulsions is measured according to an "up and down" method of shock titration (Kimball et al., 1957). An increase in seizure threshold is indicative of anti-convulsant effect. Antiepileptic drugs including the sodium channel blockers (e.g. lamotrigine) with clinically proven efficacy against generalised tonic-clonic seizures all exhibit anti-convulsant properties in this test in the mouse.

Conversely, a reduction in seizure threshold is indicative of a pro-convulsant effect as observed with known convulsant agents such as picrotoxin.

Methods

Naïve mice were acclimatised to the procedure room in their home cages, with food and water available ad libitum.

Animals were dosed i.p. according to dose group.

The vehicle (10 ml/kg i.p. 60 min pre-treatment time) was 1:1:18 vehicle 5% ethanol, 5% kolliphor EL, 90% saline.

The test compound, CBD-C6 was administered at doses of 10, 30 and 100 mg/kg given at 10 ml/kg i.p. 180 min pre-treatment time.

The positive control diazepam was used at 2.5 mg/kg (10 ml/kg i.p. 30 min pre-treatment time)

Mice were individually assessed for the production of a tonic hind limb extensor seizure using a Hugo Sachs Elec-tronik stimulator, which delivered an adjustable constant current (1-300 mA) of 0.1 s duration via corneal electrodes.

The stimulus intensity was varied by an 'up and down' method of shock titration. Thus, the first mouse within a treatment group was given a shock at the expected or estimated seizure threshold (CC$_{50}$) current, that is, the current producing tonic hind limb extensor seizure in 50% of animals. For subsequent animals, the stimulus intensity was lowered or raised in 2 mA intervals if the preceding mouse did or did not show tonic hind limb extension, respectively.

This procedure continued for all mice within the treatment group. Data generated from treatment group of n=12 was used to calculate the CC$_{50}$±s.e.m. values according to the method of Kimball et al. (1957).

Animal were culled immediately by concussion of the brain by striking the cranium, followed by dislocation of the neck.

Induction of seizure is measured as an all-or-nothing effect scored as either present (+) or absent (0) for each animal.

The data for each treatment group were recorded as the number of +'s and 0's at each current level employed and this information is then used to calculate the CC$_{50}$ value (current required for 50% of the animals to show seizure behaviour)±standard error.

Data was analysed by comparing treated groups with the appropriate vehicle control using Fisher's Exact Probability tests.

Results

FIG. 1 and Table 1 below demonstrates the data produced in this experiment.

In the vehicle group, the $CC_{50}$ value was calculated to be 21 mA.

In the diazepam (2.5 mg/kg) treated group, administered i.p. 30 minutes before the test, the $CC_{50}$ value was 29.5 mA. This result was statistically significant (p<0.001) compared to the vehicle control.

In the CBD-C6 treatment groups, administered i.p. 180 minutes before the test, the doses of 10 and 30 mg/kg CBD-C6 produced a statistically significant $CC_{50}$ value compared to vehicle.

In the mice treated with the higher doses of CBD-C6 there was a very large (376%) difference from vehicle and as such the significance value could not be calculated. However, the effect seen should be considered to be of therapeutic benefit.

TABLE 1

Evaluation of effect of CBD-C6 in the MEST test

| Treatment | Dose (mg/kg) | N | $CC_{50}$ +/− SEM | Significance | % change from vehicle |
|---|---|---|---|---|---|
| Vehicle | — | 12 | 21.0 +/− 0.5 | — | — |
| Diazepam | 2.5 | 12 | 29.5 +/− 2.4 | P < 0.001 | 40% |
| CBD-C6 | 10 | 12 | 23.4 +/− 0.9 | P < 0.05 | 11% |
| CBD-C6 | 30 | 12 | 34.3 +/− 2.8 | P < 0.001 | 63% |
| CBD-C6 | 100 | 12 | >100 | — | 376% |

Conclusions

These data demonstrate for the first time a therapeutic effect for the compound CBD-C6.

These data are significant as they provide heretofore unknown evidence that this cannabinoid which is found in minor quantities in extracts of cannabis plant may be of therapeutic value.

Example 3: Evaluation of Cannabidiol-C6 (CBD-C6) for Anticonvulsant Activity Using the Maximal Electroshock Seizure Threshold (MEST) Test in the Mouse The efficacy of CBD-C6 was tested in a mouse model of generalised seizure, the maximal electroshock seizure threshold (MEST) test as described in Example 2.

Methods

Study Details:

Naïve mice were acclimatised to the procedure room in their home cages for up to 7 days, with food and water available ad libitum.

All animals were weighed at the beginning of the study and randomly assigned to treatment groups based on a mean distribution of body weight across groups. All animals were dosed at 10 mL/kg via intraperitoneal (i.p) injection, with either vehicle, CBD-C6 at 10, 30 or 100 mg/kg, diazepam at 2.5 mg/kg or sodium valproate at 250 mg/kg.

Animals were individually assessed for the production of a tonic hind limb extensor convulsion at 60 min post-dose for vehicle, at 60, 60 and 120 min post-dose for CBD-C6 at 10, 30 and 100 mg/kg respectively, and 30 min post-dose for diazepam and sodium valproate, from a single electroshock.

The first animal within a treatment group was given a shock at the expected or estimated $CC_{50}$ current. For subsequent animals, the current was lowered or raised depending on the convulsions outcome from the preceding animal.

Data generated from each treatment group were used to calculate the $CC_{50}$±SEM values for the treatment group.

Test Compounds:

Vehicle: (5% ethanol, 5% solutol, 90% Saline) was prepared as follows: 1 mL of ethanol, 1 mL of solutol were warmed to 60° C., in 18 mL of saline (1:1:18).

Positive controls: diazepam was used at 2.5 mg/kg and sodium valproate at 250 mg/kg.

The test compound, CBD-C6 was prepared according to the method described in Example 1. CBD-C6 was administered at 10, 30 and 100 mg/kg (i.p.) in a 1:1:18 ethanol:solutol:0.9% saline formulation.

Sample Collection:

Each animal was humanely killed immediately after production of a convulsion by destruction of the brain from striking the cranium, followed by the confirmation of permanent cessation of the circulation from decapitation under The Humane Killing of Animals under Schedule 1 to the Animals (Scientific Procedures) Act 1986. Terminal blood and brain collection were performed following decapitation.

Blood was collected in Lithium-heparin tubes and centrifuged at 4° C. for 10 minutes at 1500×g. The resulting plasma was removed (>100 μL) and split into 2 aliquots of 0.5 mL Eppendorf tubes containing 100 μL of ascorbic acid (100 mg/mL) for stabilisation. Brains were removed, washed in saline and halved. Each half was placed into separate 2 mL screw cap cryovials, weighed and frozen on cardice.

Statistical Analysis

The data for each treatment group were recorded as the number of +'s and 0's at each current level employed and this information is then used to calculate the $CC_{50}$ value (current required for 50% of the animals to show seizure behaviour)±standard error.

CBD-C6 effects were also calculated as percentage change in $CC_{50}$ from the vehicle control group. Significant difference between drug-treated animals and controls were assessed according to Litchfield and Wilcoxon (1949).

Results

Table 2 below demonstrates the data produced in this experiment, and FIG. 2 illustrates these results.

In the vehicle group, the $CC_{50}$ value was calculated to be 24.3 mA.

In the positive control diazepam (2.5 mg/kg) treated group, administered i.p. 30 minutes before the test, the $CC_{50}$ value was 86.5 mA. In the sodium valproate (250 mg/kg) treated group, administered i.p. 30 minutes before the test, the $CC_{50}$ value was 281.5 mA. These results were statistically significant (p<0.001) compared to the vehicle control.

In the CBD-C6 treatment groups, administered i.p. 60, 60, and 120 minutes before the test, the doses of 10, 30 and 100 mg/kg CBD-C6 produced a statistically significant $CC_{50}$ value compared to vehicle at all three doses of the compound.

Such data are indicative that this compound will be of therapeutic benefit.

TABLE 2

Evaluation of effect of CBD-C6 in the MEST test

| Treatment | Dose (mg/kg) | N | Pre-treatment time (mins) | $CC_{50}$ ± SEM | % change from vehicle | Significance |
|---|---|---|---|---|---|---|
| Vehicle | — | 12 | 60 | 24.3 ± 0.4 | — | — |
| Diazepam | 2.5 | 12 | 30 | 86.5 ± 1.0 | 255% | $P < 0.001$ |
| Sodium Valproate | 250 | 12 | 30 | 281.5 ± 5.8 | 1057% | $P < 0.001$ |
| CBD-C6 | 10 | 12 | 60 | 30.8 ± 1.9 | 27% | $P < 0.01$ |
| CBD-C6 | 30 | 12 | 60 | 31.5 ± 1.0 | 29% | $P < 0.001$ |
| CBD-C6 | 100 | 12 | 120 | 82.5 ± 0.7 | 239% | $P < 0.001$ |

Conclusions

CBD-C6 produced a dose-related increase in MEST, which provides evidence that this compound exhibits anticonvulsive properties. Significant effects were observed at 10, 30 and 100 mg/kg, when compared to vehicle.

These data are significant as they provide heretofore unknown evidence that this cannabinoid may be of therapeutic value.

The invention claimed is:

1. A method of treating epilepsy in a subject in need thereof, comprising administering a pharmaceutical composition comprising a therapeutically effective amount of cannabidiol-C6 (CBD-C6) as the only active ingredient.

2. The method of claim 1, wherein the CBD-C6 is in the form of a plant extract.

3. The method of claim 2, wherein the CBD-C6 is in the form of a highly purified plant extract.

4. The method of claim 3, wherein the highly purified plant extract comprises at least 80% (w/w) CBD-C6.

5. The method of claim 3, wherein the highly purified plant extract comprises at least 95% (w/w) CBD-C6.

6. The method of claim 1, wherein the CBD-C6 is in the form of a synthetic compound.

7. The method of claim 1, wherein the dose of CBD-C6 is greater than 100 mg/kg/day.

8. The method of claim 1, wherein the dose of CBD-C6 is less than 100 mg/kg/day.

9. The method of claim 1, wherein the epilepsy treated is in a mammal.

10. The method of claim 9, wherein the mammal is a human.

11. The method of claim 9, wherein the mammal is a dog.

* * * * *